(12) United States Patent
Luten

(10) Patent No.: US 9,617,313 B2
(45) Date of Patent: Apr. 11, 2017

(54) PROCESS FOR PURIFYING A POLYMER MIXTURE

(75) Inventor: Jordy Luten, Nijmegen (NL)

(73) Assignee: Synthon BV, Nijmegen (NL)

( * ) Notice: Subject to any disclaimer, the term of this patent is extended or adjusted under 35 U.S.C. 154(b) by 1863 days.

(21) Appl. No.: 12/645,794

(22) Filed: Dec. 23, 2009

(65) Prior Publication Data

US 2010/0160606 A1    Jun. 24, 2010

Related U.S. Application Data

(60) Provisional application No. 61/140,751, filed on Dec. 24, 2008.

(51) Int. Cl.
*C07K 14/00* (2006.01)
*C07K 1/34* (2006.01)
*C08G 69/10* (2006.01)

(52) U.S. Cl.
CPC .............. *C07K 14/001* (2013.01); *C07K 1/34* (2013.01); *C08G 69/10* (2013.01)

(58) Field of Classification Search
None
See application file for complete search history.

(56) References Cited

U.S. PATENT DOCUMENTS

| 2,657,972 | A |   | 11/1953 | Woodward |
|-----------|---|---|---------|----------|
| 3,849,550 | A |   | 11/1974 | Teitelbaum at al. |
| 3,907,755 | A |   | 9/1975  | Margraff et al. |
| 5,800,808 | A |   | 9/1998  | Konfino et al. |
| 2006/0122113 | A1 |   | 6/2006 | Pinchasi et al. |
| 2006/0154862 | A1 | * | 7/2006 | Ray et al. ................. 514/12 |
| 2008/0021192 | A1 |   | 1/2008 | Iyer et al. |

FOREIGN PATENT DOCUMENTS

| EP | 0383620 | 8/1990 |
|----|---------|--------|
| WO | WO 2006/050122 | 5/2006 |
| WO | WO 2006/083608 | 8/2006 |

OTHER PUBLICATIONS

Millipore, "A Hands-On Guide to Ultrafiltration/Diafiltration Optimization using Pellicon Cassettes", May 2008, pp. 1-12.*

* cited by examiner

*Primary Examiner* — Lianko Garyu
(74) *Attorney, Agent, or Firm* — Mark R. Buscher

(57) ABSTRACT

A process of purifying copolymer peptides such as COP-1 polypeptides by ultrafiltration can be improved by treating the polypeptide solution with an acid before, or during the early stages of, the ultrafiltration. By adding the acid and/or forming an acid addition salts of the polypeptide before ultrafiltration is conducted permits for faster ultrafiltration. Likewise, adding the acid in the ultrafiltration process but before polypeptide precipitation or clogging occurs can also improve the efficiency/convenience of the ultrafiltration step.

10 Claims, No Drawings

PROCESS FOR PURIFYING A POLYMER MIXTURE

This application claims the benefit of priority under 35 U.S.C. §119(e) from prior U.S. Provisional Application Ser. No. 61/140,751, filed Dec. 24, 2008; the entire contents of which are incorporated herein by reference.

BACKGROUND OF THE INVENTION

The invention relates to methods for purifying polypeptide copolymers, especially COP-1 polypeptides.

Polymerization of natural or synthetic monomers is well known and described in early textbooks such as for example Organic Chemistry by Morrison and Boyd, $3^{rd}$ edition, 1980, chapter 32. Polypeptides are a specific class of polymers formed by polymerization of amino acids.

"Copolymer polypeptides" are generally formed by a random co-polymerization of amino acids. In such co-polymerization, several different amino acids having the carboxy and/or amino groups activated are mixed together under reactive conditions, whereby the peptide link formation between the various amino acids present in the reaction mixture is random. It is also known in the art that reactive chemical groups that are not part of the polymer backbone, and should remain unaltered after polymerization, should be protected by protective groups. After the polymerization is complete these protective groups are chemically removed.

A method of forming a copolymer containing leucine and phenylalanine by random polymerization is described in U.S. Pat. No. 2,657,972.

U.S. Pat. No. 3,849,550 describes a method of forming a copolymer containing alanine (A), glutamic acid (E), lysine (K), and tyrosine (Y) by random polymerization. The method uses protected side groups, followed by two deprotection steps, but does not specify any purification steps. The resulting copolymer, which has subsequently been referred to as Copolymer-1 (COP-1) (see, e.g., U.S. Pat. No. 5,800,808), was reported as having a molar ratio of A:E:K:Y of 6:2:4.5:1.

U.S. Pat. No. 5,800,808 describes methods of obtaining COP-1 having a specific molecular weight profile, with subsequent purification by dialysis or ultrafiltration. The COP-1 was reported as having a molar ratio of A:E:K:Y of 6:2:5:1. The patent does not mention industrially applicable purification methods.

WO 2006/083608 describes methods of making COP-1 and mentions ultrafiltration to remove protecting groups and low molecular weight impurities. The molar ratio in the COP-1 of A:E:K:Y corresponds to ~4.49:~1.48:~3.56:1. In an embodiment (Example 3), ultrafiltration was performed using a 5 kilodalton membrane to remove low-molecular weight impurities. After 6 cycles of ultrafiltration, the solution was acidified with acetic acid until a pH of 4.0 was achieved. Water was added and the solution was ultrafiltered until a pH of 5.5 was attained. The solution was concentrated and lyophilized for 60 hours.

US 2008/0021192 describes methods of making COP-1 and subsequently purifying the COP-1, such as by dialysis, chromatography, filtration, etc. The COP-1 reported has a molar ratio of A:E:K:Y corresponding to ~4.49:~1.48:~3.56:1. In an embodiment (scheme 5), COP-1 is purified using ultrafiltration. A reaction mixture containing the COP-1 was filtered to remove any fine insoluble materials and the filtrate was passed through an ultrafiltration using a 1 kilodalton membrane first with circulating water until a pH of 8 was observed in the permeate and then circulating with 0.3% acetic acid in water to pH 5.5-6.0 in the retentate. The solution was then lyophilized to apparently obtain COP-1 as an acetic acid salt in solid form.

The prior art COP-1 ultrafiltration purification methods described above are multistep procedures suitable for lab scale experimentation. There remains a need, however, for an easier and/or more industrially applicable ultrafiltration method for purifying complex reaction mixtures comprising polypeptides, especially COP-1.

SUMMARY OF THE INVENTION

The present invention is based on the observation that the prior art ultrafiltration processes often suffer from a clogging of the filter membrane and/or from precipitation of the copolymer polypeptide during ultrafiltration. The present invention is based in part on the discovery that providing an acid and/or forming an acid addition salt of the polypeptide early in the process can reduce or avoid such clogging and/or precipitating problems, and correspondingly the number of ultrafiltration steps and/or time required can be reduced.

Accordingly, a first aspect of the present invention relates to a process of ultrafiltration, which comprises: combining a reaction mixture having a pH of 10 or higher and containing a variety of copolymer polypeptides which collectively have more basic amino acids than acidic amino acids, with an aqueous acid solution to form a modified reaction mixture; and subjecting said modified reaction mixture to ultrafiltration to form a purified reaction mixture. The acid used can be an organic or inorganic acid and typically is an organic acid having 1 to 8 carbon atoms, more typically 1 to 4 carbon atoms, such as acetic acid. The polypeptides are generally formed from the amino acids alanine; glutamic acid and/or aspartic acid; lysine and/or arginine; and tyrosine.

Another aspect of the invention relates to a process of making purified COP-1, which comprises: (i) adding an aqueous acid solution to a reaction mixture containing unprotected COP-1 polypeptides to obtain COP-1 acid addition salts in a modified reaction mixture; and (ii) ultrafiltering said modified reaction mixture containing said COP-1 acid addition salts to form purified COP-1 acid addition salts; wherein step (i) is performed before subjecting said reaction mixture containing the unprotected COP-1 polypeptides to any ultrafiltration. The acid can be organic or inorganic as mentioned above and typically is acetic acid. The modified reaction mixture containing the COP-1 acetic acid salts preferably has a pH of less than or equal to about 10, more preferably less than about 8, such as about 4 to about 8 and in some embodiments about 5 to about 7, before the ultrafiltering of step (ii). The modified reaction mixture containing said COP-1 acetic acid salts generally has a pH that differs from the average isoelectric point of the unprotected COP-1 polypeptides by at least one pH unit. Typically, the reaction mixture containing said unprotected COP-1 polypeptides has a pH of greater than or equal to about 12 before said adding of step (i). In the usual case, the addition of the acetic acid solution lowers the pH of the reaction mixture from its typical starting value of around 12-13 to 10 or less. The concentration of said aqueous acetic acid solution is typically 0.05 to 0.5% acetic acid by volume, such as about 0.1 to 0.3%.

A further aspect of the invention relates the use of acid in such an ultrafiltration process. Specifically, in a process for purifying COP-1 polypeptides which comprises subjecting unprotected COP-1 polypeptides in a reaction mixture to ultrafiltration wherein the COP-1 polypeptides become purified in the retentate solution and the pH of the retentate decreases during the ultrafiltration, the improvement for which comprises adding an acid to the reaction mixture or retentate before or during, or both, the ultrafiltration process but not later than the retentate achieves a pH of 10.

DETAILED DESCRIPTION OF THE INVENTION

The present invention is directed to a process of purifying copolymer polypeptides such as COP-1 polypeptides by conducting ultrafiltration of the polypeptides in the presence of an acid and/or the acid addition salt form of the polypeptides. It has been discovered that adding acid and/or forming acid addition salts of the copolymer polypeptides at an early stage of the ultrafiltration, including before ultrafiltration begins, reduces or avoids the clogging of the filter membrane and/or the precipitation of the copolymer polypeptides during ultrafiltration. By providing the acid before precipitation of the copolymer polypeptide and/or clogging occurs, the process can be performed quickly and efficiently. In addition, the number of ultrafiltration steps can be reduced, e.g., there is no need for repeatedly exchanging process liquids during ultrafiltration, and fewer measurements (e.g., pH measurements) are required to determine the purification endpoint of the ultrafiltration.

The copolymer polypeptides to be purified by the invention are a mixture of various polypeptides that collectively have more basic amino acids than acidic amino acids. Often the copolymer polypeptides are formed from alanine; glutamic acid and/or aspartic acid; lysine and/or arginine; and tyrosine. Additional amino acids may also be present, but typically the copolymer polypeptides are limited to these 4 to 6 amino acids. The copolymer polypeptides are of various chain lengths, sequences, and molecular weights and collectively have an average molecular weight that is usually between 2 and 40 kilodaltons.

A preferred embodiment of the present invention relates to the purification of the copolymer polypeptides referred to as COP-1. The term "COP-1" ("Copolymer-1") refers to a mixture of polypeptides prepared from the amino acids alanine (A), glutamic acid (E), lysine (K), and tyrosine (Y). The molar ratio of A:E:K:Y in COP-1 has been variously reported. For example, the following chart illustrates the different molar ratios ascribed as being COP-1:

| Source | A:E:K:Y molar ratio |
| --- | --- |
| U.S. Pat. No. 3,849,550 | 6:2:4.5:1 |
| U.S. Pat. No. 5,800,808 | 6:2:5:1 |
| WO 2006/083608 and US 2008/0021192 | ~4.49:~1.48:~3.56:1 |
| NDA #020622 for COPAXONE ® | 4.5:1.5:3.5:1 |

For purposes of this application, the term "COP-1" polypeptides is intended to encompass all such variations in molar ratios of A:E:K:Y.

Ultrafiltration, generally, is a well-known purification/separation technique in which a solution is contacted with an ultrafiltration membrane under an applied pressure. The applied pressure can be, e.g., osmotic pressure or hydrostatic pressure. The applied pressure forces the solvent and smaller molecules through the membrane, whereas larger molecules are retained by the membrane, based on the molecular weight cutoff of the membrane. The solution passing through the membrane is called the permeate. The solution containing the retained molecules is referred called the retentate. The ultrafiltration membrane can retain particles from 1 kilodalton to 1000 kilodaltons. The ultrafiltration membrane should be inert towards the reaction mixture. Selection criteria are readily available from the membrane suppliers. The membrane preferably has a molecular weight cutoff of 1 to 10 kilodaltons, such as 3 or 5 kilodaltons. Typically, the volume of the retentate is kept constant during ultrafiltration by adding a feeding solution to the retentate. This allows better control over the ultrafiltration process and the purity of the retentate.

The ultrafiltering used in the invention typically comprises passing a reaction mixture containing copolymer polypeptides, such as COP-1, through a membrane having a molecular weight cutoff of, e.g., 1 to 10 kilodaltons, whereby the copolymer polypeptides are retained in the retentate and purified as the lower molecular weight entities are passed through the membrane. The copolymer polypeptides are "purified" in the sense that at least some amount of the unwanted residual of the reaction mixture is removed/separated from the retained copolymer polypeptides. The removal of the small molecules, such as bases and their salts, over the course of the ultrafiltration generally leads to a reduction in the pH of the initially alkaline reaction mixture or retentate.

One aspect of the invention relates to combining a reaction mixture having an initial pH of 10 or higher, preferably 12 or higher, and containing a variety of copolymer polypeptides (i.e., which collectively have more basic amino acids than acidic amino acids) with an aqueous acid solution to form a modified reaction mixture. The pH of the modified reaction mixture is generally 10 or less and sometimes 8 or less and typically in the range of 4 to 8 or 5 to 7. The modified reaction mixture is subjected to ultrafiltration to form a purified reaction mixture. For clarity, the "purified" mixture is not required to have near absolute purity, but rather need only be more pure than the starting reaction mixture. That is, by removing some of the small molecules, the remaining polypeptides are more pure and would thus be considered "purified." The "reaction mixture" is typically the resultant of the polypeptide synthesis, but in general includes any liquid containing the copolymer polypeptides for which purification of some extent is desired. For example, the reaction mixture may be concentrated or subjected to filtration including ultrafiltration before the combining step with the acid is performed. But the reaction mixture has a pH of greater than 10 at the time of the combining step. The aqueous acid solution can be based on organic or inorganic acids. The acids should normally be dissolved in the water-based solution. Typically organic acids having 1 to 8 carbon atoms are used, more typically 1 to 4 carbon atoms; i.e., formic acid, acetic acid, propionic acid, or butyric acid. While referred to herein in the singular, the term "acid" is also meant to embrace the plural form; i.e., one or more acids can be used in the solution. Generally water is the only solvent, though the use of lower alcohols or other water-miscible organic solvents is not forbidden in making the aqueous acid solution.

The two steps are often carried out sequentially wherein the acid is combined with the reaction mixture before the start of ultrafiltration. But the steps may be carried out simultaneously. That is, while the reaction mixture is undergoing ultrafiltration, an aqueous acid solution can be combined therewith to form the modified reaction mixture in situ. As long as the modified reaction mixture is formed before the pH of the reaction mixture, or more properly the retentate, is less than 10, then both steps are considered to have been carried out. This simultaneous "combining" and ultrafiltering step can be conveniently carried out if an aqueous acid solution is employed as a feeding solution in the ultrafiltration process.

Because a preferred aspect of the invention relates to a process of purifying COP-1 polypeptides by use of an acid, the invention will be further described with respect to this embodiment wherein the acid is acetic acid. It should be understood that other acids as mentioned above may be used instead of acetic acid. The process comprises adding an aqueous acetic acid solution to a reaction mixture containing unprotected COP-1 polypeptides to obtain COP-1 acetic acid salts in a modified reaction mixture and ultrafiltering said modified reaction mixture containing said COP-1 acetic acid salts to form purified COP-1 acetic acid salts, wherein the aqueous acetic acid is added (and the COP-1 acetic acid salts are formed) before subjecting the reaction mixture containing the unprotected COP-1 polypeptides to any ultrafiltration.

The aqueous acetic acid typically contains 0.05 to 0.5% acetic acid by volume in water, such as about 0.1 to 0.3% acetic acid by volume in water.

The phrase "reaction mixture containing unprotected COP-1 polypeptides" refers to a solution containing COP-1 polypeptides having substantially or practically no amino acid side groups protected by a protecting group. For example, when COP-1 polypeptides are made by random polymerization (e.g., as described in U.S. Pat. No. 3,849,550), after the amino acid side groups are deprotected, the resulting mixture is a "reaction mixture containing unprotected COP-1 polypeptides." As another example, when COP-1 polypeptides are made by recombinant DNA techniques (e.g., as described in EP 0,383,620) after the recombinant COP-1 polypeptides have been expressed in $E.\ coli$ and cleaved from the Protein A/rCOP-1 fusion protein, the resulting mixture is a "reaction mixture containing unprotected COP-1 polypeptides." Thus, the term "unprotected COP-1 polypeptides" refers both to COP-1 polypeptides that were subjected to protecting and deprotecting steps (such as in random polymerization) and to COP-1 polypeptides that have not been subjected to a protecting step (such as in recombinant DNA techniques).

In a preferred form of this embodiment, the modified reaction mixture containing the COP-1 acetic acid salts has a pH of less than or equal to about 10 before the COP-1 acetic acid salts are subject to the ultrafiltration. When the reaction mixture containing the unprotected COP-1 polypeptides has a pH of greater than 10, such as a pH of greater than or equal to about 12, the addition of the aqueous acetic acid lowers the pH to the desired pH of less than or equal to about 10. Such a high starting pH is not strictly required, however. That is, it is possible for the starting reaction mixture containing the unprotected COP-1 polypeptides to have a pH of less than 10 before the aqueous acetic acid is added. Nonetheless, the typical embodiment of the invention does use a reaction mixture having a pH of around 13 and the addition of the acetic acid thereto reduces the pH to about 10 or less. In some of these embodiments, the pH of the modified reaction mixture prior to ultrafiltration is less than 8, such as a pH of about 4 to about 8 or even about 5 to about 7. The resulting modified reaction medium having such a reduced pH is then subjected to ultrafiltration in order to purify the COP-1 acetic acid salts.

Ultrafiltration of polypeptides can suffer from a concentration gradient towards the membrane interface, known as concentration polarization. Concentration polarization has a negative effect on the flux (mass transport over the membrane). Also, the ion strength of the retentate affects the flux. Fluxes are generally higher at low ion strength and lower near the isoelectric pH of the polypeptide(s) being ultrafiltered. High ion strength also results in high osmotic pressure which may contribute to a lower flux. The isoelectric point of an amino acid is the pH at which the amino acid is present as its dipolar form, fully ionized but with no net electric charge. The isoelectric point of a polypeptide is the pH at which the polypeptide has no net electric charge. The average isoelectric point of a mixture of polypeptides is an average of the isoelectric points of the polypeptides contained in the mixture.

COP-1 polypeptides, collectively, have more basic amino acids than acidic amino acids, and the average isoelectric point for COP-1 polypeptides is typically higher than about 7, e.g., between about 8 and about 11, such as about 9 or about 10, depending on the actual ratio between basic and acidic amino acids present in the COP-1 polypeptides, collectively. Advantageously, the modified reaction mixture containing the COP-1 acetic acid salts has a pH that differs from the average isoelectric point of the unprotected COP-1 polypeptides by at least one pH unit, since the mass transport over the membrane (flux) is lowest in the isoelectric pH. It appears that the presence of the acetic acid anions in the modified reaction mixture/retentate prevents or reduces precipitation of the polypeptides as the mixture/retentate passes through the pH corresponding to the isoelectric point or other precipitation point of the unprotected COP-1 polypeptides.

A feeding solution is typically used during the ultrafiltration. When supplied, the feeding solution is normally an aqueous solution of the same acid as used for adjusting the pH, e.g., an aqueous acetic acid. For clarity, in other preferred embodiments of the invention, the feeding solution is used as the aqueous acid solution in the combining or adding step. Preferably, the concentration of an aqueous acetic acid feeding solution is from about 0.05 to 0.5% by volume, such as about 0.1 to 0.3% by volume. Higher concentrations of acetic acid can result in a less effective removal of acetic acid during subsequent isolation (lyophilization) steps. Optionally, the feeding solution can be changed to water in the later stages of the ultrafiltration process to remove excess acetic acid; for example, once the pH is less than 6. The concentration of acetic acid in the reaction mixture typically does not exceed the concentration of acetic acid in the feeding solution.

The volume/rate of addition of the feeding solution is typically adjusted to achieve a concentration of COP-1 acetic acid salts in the retentate at about 1 to 50 grams per liter during ultrafiltration, often 20 to 50 grams per liter, though higher concentrations can be used. During ultrafiltration the concentration should generally not be higher than about 100 gram per liter and concentrations of around 250 gram per liter or higher should be avoided. These higher concentrations may have a negative effect on the flux.

Upon completion of the ultrafiltration step, the retentate (modified reaction mixture) containing the purified COP-1 polypeptides (purified COP-1 acetic acid salts) has a pH between 5 and 7, such as about 5.5 to about 6. Advantageously, the ultrafiltration can be performed for 20 hours or less, preferably 10 hours or less, and more preferably 5 hours or less. The concentration of the purified COP-1 polypeptides in the retentate upon completion is typically about 2 to about 50 grams per liter, generally 20 to 50 grams per liter, though higher concentrations can be obtained such as 75 grams per liter.

In a preferred embodiment, the purified COP-1 polypeptides have an average molecular weight of 4 to 11 kilodaltons (such as 5 to 9 kilodaltons or 6 to 10 kilodaltons) or 7 to 12 kilodaltons. Typically, less than 5 weight % of the purified COP-1 polypeptides have a molecular weight of more than 40 kilodaltons. Preferably, a molar fraction of COP-1 polypeptides having a molecular weight of 2 to 20 kilodaltons in said purified COP-1 polypeptides is at least 0.75. The term "molar fraction" is the number of moles of a component substance in a mixture divided by the total number of moles in the mixture.

COP-1 polypeptides suitable for use in the purification process of the present invention can be made using known methods. For example, COP-1 polypeptides, including COP-1 polypeptides having a specific molecular weight profile, are commonly made by random polymerization such as shown in U.S. Pat. No. 5,800,808 and US 2008/0021192. A method of preparing COP-1 polypeptides using recombinant DNA technology, however, is also known as described in EP 0 383 620.

Thus, the purification process of the present invention can further include steps directed to making the unprotected COP-1 polypeptides by random polymerization. In particular, the purification process can further comprise polymerizing a mixture of N-carboxyanhyrides of alanine, protected glutamic acid, protected lysine, and tyrosine to form protected COP-1 polypeptides and treating the protected COP-1 polypeptides with at least one deprotecting agent to obtain the unprotected COP-1 polypeptides. The protected glutamic acid can be formed using, for example, a benzyl or a methoxy protecting group. On the other hand, the protected lysine can be formed using, for example, a cyclic imide or a t-butoxycarbonyl protecting group.

The molecular weight distribution of the COP-1 polypeptides is influenced by several factors, such as the concentration of the polymerization-initiator, the reaction temperature, and the reaction time. After the polymerization reaction is terminated, the resulting polypeptide mixture can be subjected to, for example, acid or alkaline hydrolysis to obtain a lower average molecular weight with a broader molecular weight distribution, such as COP-1 polypeptides having the molecular weight profiles described above. Various other methods for obtaining a desired molecular weight profile are known in the art.

Deprotecting agents suitable for use with corresponding protecting agents are known in the art. For example, a benzyl ester protecting group can be removed from a protected glutamic acid after polymerization by suitable acids, such as 33% hydrobromic acid in acetic acid, which is preferably bromine free. Such an acid deprotection step can also conveniently be used as a depolymerization step, so that deprotection and depolymerization are combined in one step. As another example, trifluoroacetyl protective groups can be removed from a protected lysine with an organic base, such as piperidine. Typically, a first deprotecting agent is used to remove the protecting groups from glutamic acid residues (such as 33% hydrobromic acid), and then a second deprotecting agent is used to remove the protecting groups from lysine residues (such as piperidine). The phrase "treating said protected COP-1 polypeptides with at least one deprotecting agent to obtain said unprotected COP-1 polypeptides" includes multiple deprotecting steps using different deprotecting agents, as well as a single deprotecting step or multiple deprotecting steps using the same deprotecting agent.

Optionally, the purified COP-1 polypeptides can be isolated from the retentate. For example, the purification process of the present invention can further comprise lyophilizing the purified COP-1 polypeptides in salt form after ultrafiltration. In this way, solid COP-1 polypeptide acetates can be obtained. Lyophilization also allows for the removal of excess acetic acid used in the ultrafiltration.

The above preferred embodiment relates to sequentially carrying out the steps of combining the acid with the polypeptide followed by ultrafiltering, optionally with additional acid as a feeding solution. But in another preferred embodiment, these steps can be carried out simultaneously or in overlapping fashion. The acetic acid solution can be combined with the reaction mixture as the feeding solution at the start of the ultrafiltration, or, during the ultrafiltration. In this embodiment, the acid should be combined with the reaction mixture no later than the isoelectric point or other pH point at which precipitation of the polypeptide occurs, i.e., added before precipitation of the polypeptide, and generally by no later than a pH of 10. For a COP-1 reaction mixture, the acid is typically combined by no later than a pH of around 12. The other conditions as expressed above equally apply to this embodiment.

Although the description above focused primarily on purifying COP-1 polypeptides using acetic acid and the salts thereof, the present invention is not so limited and the steps and conditions of ultrafiltration, including the feeding solution, etc., as expressed above are generally applicable to all aspects of the invention. Likewise, the COP-1 polypeptides could also be purified using other acid solutions and their corresponding acid addition salts. Similarly, besides COP-1 other polypeptides as described previously herein can be purified in like manner as described for COP-1.

The invention will be further described with reference to the following non-limiting examples.

EXAMPLES

Example 1

A polypeptide was prepared as described in U.S. Pat. No. 3,849,550. The resulting reaction mixture, a 50 milliliter solution (1M piperidine) containing 1.0 gram of trifluoroacetyl protected polymer, was diluted to 500 mL with 0.3 percent by volume acetic acid in demineralized water. The pH of the resulting solution is around 10. The diluted solution was put into the reservoir of a Millipore Labscale TFF system, equipped with a 5 kDa Pellicon XL filter (PLCCC 5, 50 cm$^2$) membrane. Under selected conditions (pressure inlet 30 psi, pressure outlet 10 psi, permeate flow 100 mL/h), 0.3% acetic acid in demineralized water was used as a feeding solution to purify the polymer. After 16 hours the retentate had a pH of about 5, the feeding was stopped, and the retentate was ultra filtrated for an additional 4 hours to increase the concentration of polypeptide in the retentate to about 20 grams per liter. The total run time was 20 hours.

Example 2

As a comparative example the same procedure was followed as in Example 1, but the reaction mixture was diluted with demineralized water and demineralized water was used as the feeding solution during ultrafiltration. After about 2 or 3 hours polymer aggregates were formed when the retentate reached a pH of about 8 or 9. These aggregates appeared to block the filter, resulting in an increased membrane pressure of more than 4 bar, which was above the safety specifications indicated by the supplier. The feeding solution was then immediately switched to 0.3 percent by volume acetic acid, and ultrafiltration was continued until the pH of the retentate was about 5. The total run time increased from 20 to 24 hours.

A comparison of the examples shows advantages of the method according to the invention. Besides omitting one feeding solution change, the total run time was decreased significantly because precipitation of the polypeptide was reduced or prevented. Surprisingly, no precipitation or aggregation was observed in Example 1 when the retentate passed through the isoelectric point of the polypeptide. Furthermore, in Example 1 the risk of membrane damage was reduced or eliminated. This is advantageous because when a membrane is operated outside the specified safety pressure limits it needs to be checked after the ultrafiltration run is completed. When damaged, the ultrafiltration run has to be repeated.

Each of the patents, patent applications, and brochures mentioned above are incorporated herein by reference. The invention having been described it will be obvious that the same may be varied in many ways and all such modifications are contemplated as being within the scope of the invention as defined by the following claims.

I claim:

1. A process of making purified Copolymer-1 (COP-1), which comprises:
   (i) adding an aqueous acid solution to a reaction mixture containing unprotected COP-1 polypeptides to obtain COP-1 acid addition salts in a modified reaction mixture; and
   (ii) ultrafiltering said modified reaction mixture containing said COP-1 acid addition salts to form purified COP-1 acid addition salts;
wherein said adding step (i) is performed before subjecting said reaction mixture containing the unprotected COP-1 polypeptides to any ultrafiltration; and wherein said ultrafiltering step (ii) is carried out with the addition of an aqueous acid feeding solution to said modified reaction mixture.

2. The process according to claim 1, wherein said acid in said aqueous acid solution is acetic acid and said COP-1 acid addition salts are COP-1 acetic acid addition salts.

3. The process according to claim 2, wherein said modified reaction mixture containing said COP-1 acetic acid salts has a pH of less than or equal to about 10 before said ultrafiltering of step (ii).

4. The process according to claim 3, wherein said modified reaction mixture containing said COP-1 acetic acid salts has a pH of about 4 to about 8 prior to said ultrafiltering of step (ii).

5. The process according to claim 3, wherein said reaction mixture containing said unprotected COP-1 polypeptides has a pH of greater than or equal to about 12 before said adding of step (i).

6. The process according to claim 2, wherein said ultrafiltering is performed until the modified reaction mixture containing the COP-1 acetic acid salts has a pH of 5 to 7.

7. The process according to claim 2, wherein said ultrafiltering is performed for not more than 20 hours, and the concentration of the COP-1 acetic acid salts in said modified reaction mixture after said ultrafiltering is about 2 to about 50 grams per liter.

8. The process according to claim 2, wherein said purified COP-1 polypeptides have an average molecular weight of 4 to 11 kilodaltons.

9. The process according to claim 1, wherein said aqueous acid solution and said aqueous acid feeding solution are each 0.05 to 0.5% by volume acetic acid solutions.

10. The process according to claim 1, wherein said purified COP-1 acid addition salts are in a concentration of about 2 to about 50 grams per liter.

* * * * *